US00RE37670E

(19) United States
(12) Reissued Patent
Nau et al.

(10) Patent Number: US RE37,670 E
(45) Date of Reissued Patent: Apr. 23, 2002

(54) ANTIPROLIFERATIVE AND NEUROTROPHIC MOLECULES

(75) Inventors: Heinz Nau, Berlin (DE); Ciaran M. Regan, Dublin (IE)

(73) Assignee: American Biogenetics Inc., Copiague, NY (US)

(21) Appl. No.: 09/250,001

(22) Filed: Feb. 8, 1999

Related U.S. Patent Documents

Reissue of:
(64) Patent No.: 5,672,746
Issued: Sep. 30, 1997
Appl. No.: 08/298,108
Filed: Aug. 30, 1994

(51) Int. Cl.[7] ..... C07C 57/02
(52) U.S. Cl. ..... 562/598; 562/493; 562/495; 562/606; 562/512.2
(58) Field of Search ..... 562/493, 495, 562/598, 606, 512.2

(56) References Cited

U.S. PATENT DOCUMENTS

| | | | | |
|---|---|---|---|---|
| 3,325,361 | A | 6/1967 | Meunier | 167/65 |
| 3,701,729 | A | 10/1972 | Fischer et al. | 252/1 |
| 3,847,956 | A | 11/1974 | Silbert et al. | 260/413 |
| 3,932,285 | A | 1/1976 | Ceprini et al. | 252/1 |
| 4,025,649 | A | 5/1977 | Taillandier et al. | 424/318 |
| 4,129,599 | A | 12/1978 | Escher et al. | 260/586 |
| 5,021,398 | A | 6/1991 | Sharma et al. | 501/1 |
| 5,503,830 | A | 4/1996 | Nekrasov et al. | 424/193.1 |
| 5,681,854 | A | 10/1997 | Pang et al. | 514/557 |

FOREIGN PATENT DOCUMENTS

| | | |
|---|---|---|
| EP | 0 632 008 B1 | 4/1998 |
| FR | 2599737 | 12/1987 |
| JP | 56-80116 | 7/1981 |
| JP | 59-67266 | 4/1984 |
| JP | 1-135740 | 5/1989 |
| JP | 6-188152 | 7/1994 |
| WO | WO 94/06456 | 3/1994 |
| WO | WO 94/06743 A1 * | 3/1994 |
| WO | 94/06743 | 3/1994 |
| WO | WO 94/12608 | 6/1994 |
| WO | WO 95/33044 | 12/1995 |
| WO | WO 98/03472 | 1/1998 |

OTHER PUBLICATIONS

Chem. Abst. 115:149747 (1991).
R.S. Hauck et al., "On the development of alternative antiepileptic drugs. Lack of enantioselectivity of the anticonvulsant activity, in contrast to teratogenicity, of 2–n–propyl–4–pentenoic acid and 2–n–propyl–4–pentynoic acid, analogs of the anticonvulsant drug valproic acid." *Naturwissenschaften* 78:272–274 (1991)
Doyle, et al. (1993) *J. Neurochem.* 61:266–272.
Doyle and Regan (1993) *J. Neural Transm.* 92:33–49.
Haj–Yehia, Abdulla and Bialer, Meir (1990) *J. Pharm. Sci.* 79:8, 719–724.
Hauck and Nau (1989) *Toxicol. Lett.* 49:41–48.
Hauck, et al. (1992) *Toxicol. Lett.* 60:145–153.
Kurth, Mark J. and Brown, Edward G., (1987) *J. Am. Chem. Soc.,* 109(22), 6844–5.
Kurth, Mark J., et al., (1988) *Tetrahedron Lett.,* 29(13), 1517–1520.
Löscher, W. and Nau, H., (1985) *Neuropharmacology* 24:5, 427–435.
Maguire, C. and Regan, C.M., (1991) *Int. J. Devl. Neuroscience* 9:6 581–586.
Martin, M.L. and Regan, C.M., (1991) *Brain Research*, 554:223–228.
Martin, M.L. and Regan, C.M., (1988) *Brain Research*, 459:131–137.
Martin, et al., (1988) *Toxic in vitro*, 2:1 43–48.
Nau, H. and Löscher, W., (1986) *Fund. Applied Toxicol.* 6:669–676.
Nau, et al., (1981) *J. Pharmacol. Exp. Ther.* 219:768–777.
Nau, et al., (1991) *Pharmacol. and Toxicol.* 69:310–321.
Okada, Katsuhide, et al., (1980) *Agric. Biol. Chem.,* 44(11), 2595–2599.
Regan, C.M., *Brain Research*, 347:394–398.
Regan, et al. (1991) *Toxic. in vitro* 5:77–82.
Rougon, et al., (1986) *J. Cell Biol.* 103:2429–2437.
Wilson, Stephen R., (1993) *Proc. Workshop Vitam. D., 6th(Vitam. D)*, 749–754, New York University, NY, NY 10003.
Atkinson, R.S., et al., Intramolecular Reactions of N–Nitrenes: Description of the Transition State Geometry for Addition to Alkenes, *J. Chem. Soc., Perkin Trans.* 1:1135–45 (1987).
Atkinson, R.S., et al., Intramolecular Reactions of N–Nitrenes with Alkenes, *J. Chem. Soc., Perkin Trans.* 1:1905–12 (1984).
Barton, H, et al., Photochemical Degradation of Barbituric Acid Derivatives, *Pharmazie*, 38:630–1 (1983).
Baxter, G.P.,. Thirty–Sixth Annual Report of the Committe on Atomic Weights. Determinations Published During 1929, *J. Am. Chem. Soc.,* 52:1281–1283 (1930).
Borstlap, C., 2–Alkylalkanoic Acids: Relation Between Structure and Sensitivity Towards Water Hardness, *Chem Phys. Chem. Anwendungstech. Grenzflaechenaktiven Stoffe, Ber. Int. Knogr., 6th*, 1:91–9 (1973).
Breusch, F.L., et al., Isomeric Series of the Di–N–Alkylacetic Acids $C_{23}H_{46}O_2$, *Second Chemical Institute of the University of Istanbul, Series C.*, 33:39–42 (1968).
Chapman, A.G., et al., Acute Anticonvulsant Activity of Structural Analogues of Valproic Acid and Changes in Brain Gaba and Aspartate Content, *Life Sciences*, 32:2023–2031 (1983).
Curran, D.P., et al., Amide–Based Protecting/Radical Translocating (PRT) Groups. Generation of Radicals Adjacent to Carbonyls by 1,5–Hydrogen Transfer Reactions of O–Iodoanilides, *Tetrahedron*, 50:7343–66 (1994).

(List continued on next page.)

*Primary Examiner*—Dwayne C. Jones
(74) *Attorney, Agent, or Firm*—Morgan & Finnegan, LLP

(57) ABSTRACT

Neurotrophic and antiproliferative compounds related to the antiepileptic drug valproate are provided. These compounds are useful for promoting neuronal function as in neurodegenerative disorders and for treating neoplastic disease.

8 Claims, 3 Drawing Sheets-

OTHER PUBLICATIONS

Figure 1:
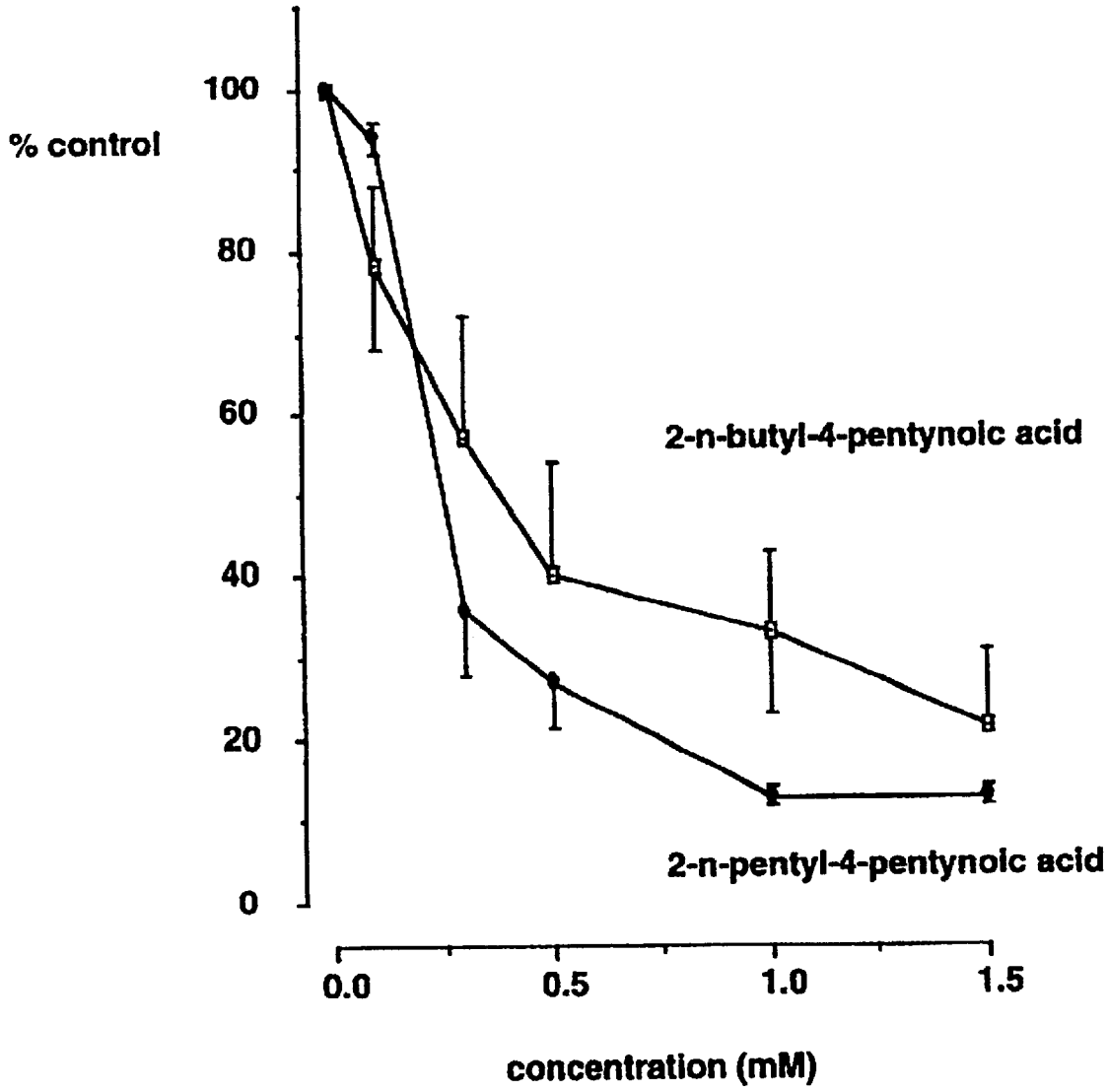
Figure 2A:
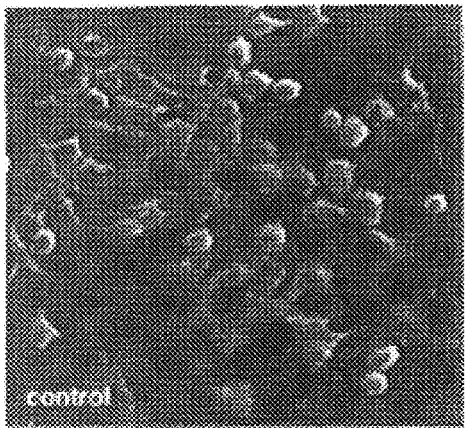
Figure 2B:
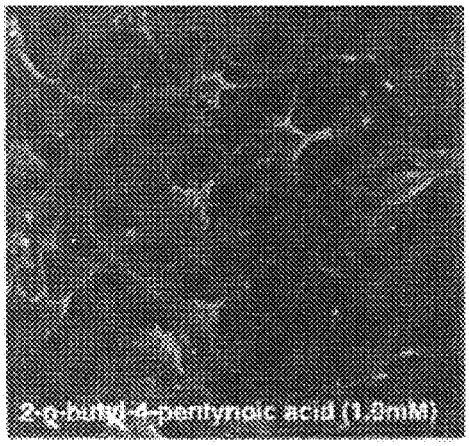
Figure 2C:
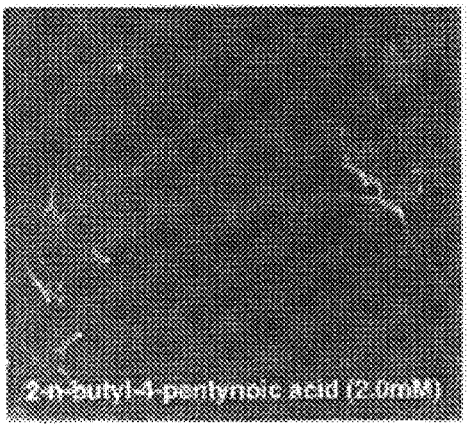
Figure 2D:
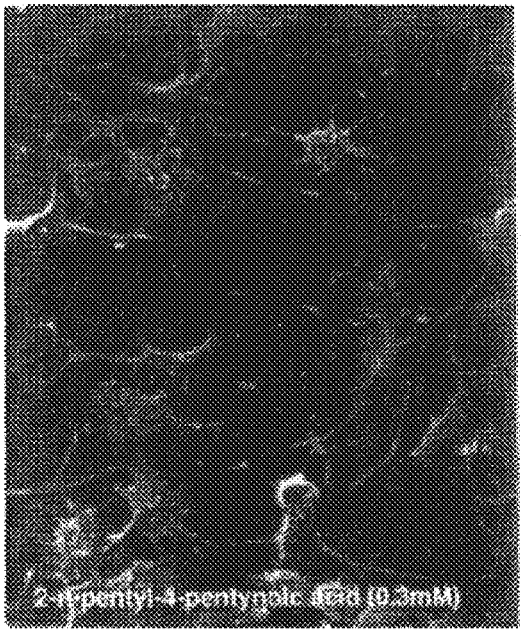
Figure 2E:
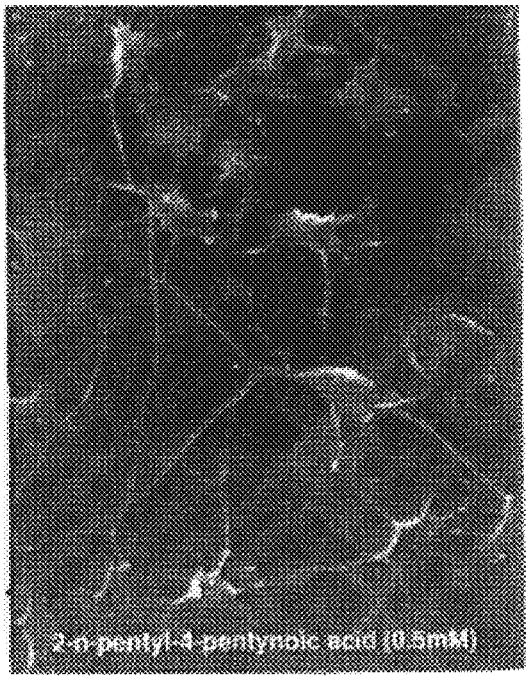

Drake, C.A ., et al., Synthesis of Ethylenes with Acyclic Quaternary Carbons by Dehydration of Neopentyl Alcohols. Application of the 2–D Inapt Technique, *J. Org. Chem.,* 53:4555–62 (1988).

Fu, G.C., et al., Catalytic Ring–Closing Metathesis of Functionalized Dienes by a Ruthenium Carbene Complex, *J. Am. Chem. Soc.* 115:9856–7 (1993).

Gavrilova, V. M., et al., Side Reactions in Hydrocarboxylation of Olefins, Translated from *Zhurnal Prikladnoi Khimii,* 63:1428–1431 (1990).

Kato, K., et al., Thromboxane Synthetase Inhibitors (TXSI). Design, Synthesis, and Evaluation of a Novel Series of $_{\omega}$–Pyridylalkenoic Acids, *J. Med. Chem.,* 28:287–94 (1985).

Keane, P.E., et al., The Effects of Analogues of Valproic Acid on Seizures Induced by Pentyleneterazol and Gaba Content in Brain of Mice, *Neuropharmacology.* 22:875–879 (1983).

Konen, D.A., et al., $_{\alpha}$ Anions. VII. Direct Oxidation of Enolate Anions to 2–Hydroperoxy–and 2–Hydroxycarboxylic Acids and Esters, *J. Org. Chem.,* 40:3253–8 (1975).

Kotva, R., et al., Some 2–Substituted Derivatives of 5–(2–Amino–6–Hydroxy–4–Oxo–3, 4–Dihydro–5–Pyrimidinyl)–Pentanoic Acid, *Collection Czechoslovak Chem. Commun.* 46:1397–404 (1981).

Kurata, K., et al., Synthesis of Alkl–3 $_{\delta}$–Lactones v. Synthesis of Alkyl–3 $_{\delta}$–Lactones, *Chem. Pharm. Bull.,* 24:538–40 (1976).

Kurth, M.J., et al., Regioselectivity in the Iodolactonization of 1,6–Heptadien–4–Carboxylic Acid Derivatives, *Tetrahedron Lett.,* 29:1517–20 (1988).

Lambert, C., et al., Palladium (II) Catalyzed Cyclization of Alkynoic Acids, *Tetrahedron Lett.,* 25:5323–6 (1984).

Lindau, J., et al., Thermal Phase Behaviour of Thallium (L) Branched Alkanoates—Influence of Chain Length and Position of Branching on the Occurence of the (Anhydrous) Neat Phase; *Mol. Cryst. Liq. Cryst.,* 133:259–66 (1986).

McCarty, F.J., et al., Synthesis and Pharmacology of a Series of 1–Aralykyl–3–Butenylamines, *J. Med. Chem.,* 11:534–41 (1968).

Mellow, A.M., et al., Sodium Valproate in the Treatment of Behavioral Disturbance in Dementia, *J. Geriatric Psychiatry and Neurology*, 6:205–209 (1993).

Mysak, A.E., et al. Gas–Chromatographic Analysis of Branched Carboxylic Acids Formed on Carboxylating $C_6$–$C_{10\alpha}$–Olefins, *Journal of Analytical Chemistry of the USSR*, 25:1729–1731 (1970).

Negrete, G.R., et al.; Asymmetric Alkylations of N–Acyl Dihydropyrimidinones; *Tetrahedron Asymetry* 2:105–108 (1991).

Padwa, A., et al., Ligand Effects on Dirhodium (II) Carbene Reactivities. Highly Effective Switching Between Competitive Carbenoid Transformations, *J. Am Chem. Soc.,* 115:8669–80 (1993).

Sangster, J., Octanol–Water Partition Coefficients of Simple Organic Compounds, *J. Phys. Chem.* 18:1111–1229 (1989).

Saus, A., et al., On The Preparation of the Stereoisomeric Hydroxymethylpentadecanes, *Tenside*, 6:129–30 (1969).

Shostenko, A.G., et al., Radiation–Induced Interaction of Ethylene wtih Carboxylic Acids, Translated from *Khimiya Vyzokikh Energii* [*High–Energy Chemistry*] 10:371–373 (1976).

Sonnet, Philip E., Synthesis of the Stereoisomers of the Sex Pheromones of the Southern Corn Rootworm and Lesser Tea Tortrix, *J. Org. Chem.,* 47:3793–6 (1982).

Spencer, R. W., et al., Ynenol Lactones: Synthesis and Investigation of Reactions Relevant to their Inactivation of Serine Proteases, *J. Am. Chem. Soc.,* 108:5589–97 (1986).

Stéllberg, G.; Syntheses of Substituted Glycerol Ethers; *Chemica Scripta*, 7:31–41 (1975).

Staninets, V.I., et al., Conformational Effects in Iodolactonization of Anions of $_{\alpha}$–R–Allylacetic Acids, Translation of *Dokl. Akad. Nauk SSSR*, 187:109–111 (1969) @ 525–527 of the English Edition of that Journal.

Yoshishu, K., et al., The Proceedings for the 23$^{rd}$ Symposium on Essences, Terpenes and Essential–Oil Chemistry, *Koryo, Terupen oyobi Seiyu Kagaku ni kansuru Toronkai*, 23$^{rd}$, 157–8 (1979).

Zambelli, A., et al., Carbon–13 Nuclear Magnetic Resonance Analysis of Model Compounds of Saturated End Groups in Polypropylene, *Macromolecules*, 12:154–6 (1979).

Nau et al., "Valproic Acid–Induced Neural Tube Defects in Mouse and Human: Aspects of Chirality, Alternative Drug Development, Pharmacokinetics and Possible Mechanisms", Pharmacology & Toxicology 69, pp. 310–321, 1991.*

* cited by examiner

ANTIPROLIFERATIVE AND NEUROTROPHIC MOLECULES

Matter enclosed in heavy brackets [ ] appears in the original patent but forms no part of this reissue specification; matter printed in italics indicates the additions made by reissue.

FIELD OF THE INVENTION

This invention provides methods and compositions useful for the prevention and/or treatment of neurodegenerative and proliferative diseases. The compositions of the invention promote neuronal cell maturation and retard their proliferation. In particular, this invention relates to nonprotein neurotrophic molecules capable of passing the blood brain barrier to provide therapeutic effects.

BACKGROUND

Proper function of the nervous system requires the maturation and maintenance of neuronal cells. In addition, the establishment of proper synaptic connections allows for the communication between different neurons. Defects in the survival of neurons, or the ability to maintain synaptic connections is associated with neurodegenerative disorders including Alzheimer's disease, Huntington's disease, amyotrophic lateral sclerosis (ALS), Parkinson's disease, stroke and degeneration of neurons due to diabetic neuropathy and trauma.

Many of the neurodegenerative disorders are associated with the loss or degeneration of a particular class of neuronal cells. For example, in Parkinson's disease dopaminergic neurons of the substantia nigra degenerate. Whereas ALS is associated with the loss of motor neurons. Wernicke-Korsakoff syndrome, commonly associated with chronic alcoholism, causes amnesia due to damage to the mammillary bodies and medial dorsal nucleus of the thalamus. Butters N., Seminar Neurol. (1984) 4:226–244. Alzheimer's disease appears to be associated with the degeneration of certain cholinergic neurons. The severance of axons as a result of trauma may cause retrograde degeneration and neuronal death.

The association between neurodegeneration and the development of disease has prompted the search for neurotrophic agents capable of retarding, preventing, or reversing such neurodegeneration. To date, much emphasis in this area has focused on the identification and characterization of neurotrophic polypeptides. For example, attention has been given to studying the effects of nerve growth factor (NFG), ciliary neurotrophic factor (CNTF), brain drive neurotrophic factor (BDNF) and others. The general neurotrophic effect of CNTF and, in particular, its trophic action on motor neurons has led to its investigation as a useful agent in the treatment of ALS and other neurodegenerative disorders. See, for example, Collins et al. U.S. Pat. No. 5,141,856 and Masiakowski WO 91/04316 which are incorporated herein by reference. NGF which has been shown to promote neuronal outgrowth from central cholinergic neurons has been suggested as a useful agent in the treatment of Alzheimer's disease. Most of the neurotrophic polypeptides identified to date are active on relatively restricted populations of neuronal cells. Whereas others such as CNTF are active on a greater number of neuronal cell types.

It has generally been observed that agents which induce maturation or differentiation of neuronal cells in culture, also inhibit their proliferation. Normal proliferating embryonic precursors to sympathetic and sensory neurons are induced to mature and stop dividing in the presence of certain growth factors such as NGF. The association between neuronal maturation or differentiation and anti-mitotic action has also been observed for certain neoplastic cells which are responsive to neurotrophic factors. For example, rat pheochromocytoma, PC12, cells in the presence of NGF develop long neurites and stop dividing. Green LA and Tischler AS, Proc. Natl. Acad. Sci. USA (1976) 72:2424–2428. Similar effects have been observed with other neuronal cells.

Cells in the nervous system give rise to a variety of potentially fatal neoplastic diseases. For example, neuroblastoma and pheochromocytoma are believed to arise from cells having an origin in the neural crest. Non-neuronal cells of the nervous system including glial cells, astrocytes and Schwann cells also give rise to different types of tumors. Most present agents used for chemotherapy involving neuronal cells are cytotoxic and have relatively poor specificity and penetrability. Treatment of neoplastic disease through agents causing maturation has been a long sought for goal. Aaronson, S. A. Science (1991) 254:1146–1153.

Although neurotrophic polypeptides may eventually prove useful for treating certain neurodegenerative, and proliferative disorders, they are characterized by poor bioavailability resulting from their relatively large size making them resistant to passing through the blood brain barrier. This poor penetration into the relevant target tissue raises substantial difficulties in their use for treating neurodegenerative disorders and neoplastic disease of the central nervous system.

The anticonvulsant sodium valproate (VPA) is a branched chain carboxylic acid effective in the treatment of primary generalized seizures, especially those of the absence type. Pinder, R. M. et al., Drugs (1977) 13:81–12. Recently, VPA has been reported to be a teratogen and has been suggested as potentially causing neural tube defects in 1% to 2% of exposed fetuses (Robert E. and Rosa F. W., "Maternal valproic acid and neural tube defects," Lancet (1982) 2:937). In addition, a number of other defects are also induced by valproic acid treatment during pregnancy (Nau et al. J. Pharmacol. Exp. Ther. (1981) 219:768–777. Spina bifida aperta, a most serious birth defect, can now also be induced by valproic acid in an animal model (Ehlers et al., 1992 a,b). Like the neurotrophic polypeptides, valproic acid also shows very limited transfer into the central nervous system of the human (Löscher et al., Epilepsia (1988) 29:311–316). For reviews of clinical and experimental valproic acid teratogenesis. cf. Nau et al., Pharmacol. Toxicol. (1991) 69:310–321; Nau, CIBA Foundation Symposium 181, pp. 615–664; Marcel Dekker, 1993.

Studies in vitro have demonstrated valproate to potently inhibit the rate of neural derived cell proliferation at concentrations within its therapeutic plasma level (Regan, C., Brain Res. (1985) 347:394–398). This antiproliferative action of valproate is restricted to a defined point in the $G_1$ phase of the cell cycle. Martin M. and Regan C., Brain Res. (1991) 554:223–228. In the presence of valproate, cells assume a differentiated phenotype as judged by morphology, increased cell-substratum adhesivity and decreased affinity for concanavalin A lectin coated surfaces (Martin et al., Toxic in Vitro (1988) 2:43–48; Martin et al., Brain Res. (1988) 459:131–137; Maguire and Regan, Int. J. Devl. Neurosci. (1991) 9:581–586; Regan, C., Brain Res. (1985) 347:394–398. These actions of valproate are likely to be restricted to cells of the developing neural tube as, in in vivo experimental models, valproate has been shown to increase the incidence of neural tube defects and sequester specifically into the neuroephithelium where it generates cellular disarray (Dencker et al., Teratology (1990) 41:699–706; Ehlers et al., Teratology (1992) 45:145–151; Ehlers et al., Teratology (1992) 46:117–130; Kao et al., Teratogen. Mutagen, Carcinogen. (1981) 1:367–382; Turner et al., Teratology (1990) 41:421–442.

Hyperthermia, which induces neural tube defects (Chernoff and Golden, Teratology (1988) 37:37–42; Edwards, Teratogen. Mutagen. Carcinogen. (1986) 6:563–582; Shiota, Am J. Med. Genet. (1982) 12:281–288; Finnell et al., Teratology (1986) 33:247–252), also arrests neural cells in the $G_1$ phase of the cell cycle both in vivo and in vitro (martin et al. Brain Res. (1991) 554:223–228; Walsh and Morris, Teratology (1989) 40:583–592); and produces similar pro-differentiative effects to those observed with valproate (Martin and Regan, Brain Res. (1988) 459:131–137). Thus, a coincident anti-proliferative and pro-differentiative action may identify agents which are capable of inducing neural tube defects yet provide a basis for the development of compounds useful for treatment or prevention of neurodegenerative diseases.

The studies of the structure activity relationship of teratogenic valproate-related compounds suggest a strict structural requirement for high teratogenic potency. Nau, H. et al., Pharmacol. & Toxicol. (1991) 69:310–321. Studies of structure-activity relationships were possible as a result of previous work demonstrating that the parent drug molecule—at least in the case of valproic acid—and not metabolite(s) proved responsible for the teratogenic action (Nau, Fundam Appl Toxicol, (1986) 6:662–668. Molecules which are highly teratogenic were reported to require an alpha-hydrogen atom, a free carboxyl function, and branching on carbon atom 2 with two chains containing three carbons each for maximum teratogenic activity. (Nau and Löscher, 1986, Nau and Scott, 1986). Substances which do not conform with these strict structural requirements are of very low or negligible teratogenic activity, but still often exhibit good anticonvulsant activity in several experimental models. These compounds may therefore be valuable anti-epileptic agents (Nau et al., Neurology (1984) 34:400–402; Löscher and Nau, Neuropharmacol (1985) 24:427–435; Wegner and Nau, Neurology (1992) 42 (Supp. 5):17–24; Elmazar et al., J. Pharm. Sci. (1993) 82:1255–1258. Teratogenic activity also demonstrated stereoisomeric preferences suggesting a stereoselective interaction between the drugs and a specific structure within the embryo.

In the case of 4-en-VPA (2-n-propyl-4-pentenoic acid) (Hauck and Nau, Toxicol Lett (1989) 49:41–48) and 4-yn-VPA (2-n-propyl-4-pentynoic acid) (Hauck and Nau, Pharm. Res. (1992) 9:850–855) the S-enantiomers proved to be more potent teratogens than the corresponding R-enantiomers. This stereoselective teratogenicity was due to differing intrinsic teratogenic potencies of the enantiomers, and not due to differences in pharmacokinetics as both enantiomers of a given pair reached the target tissue to the same degree, but one was more potent than the other (Hauck et al., Toxicol. Lett (1992) 60:145–153). Other examples supported the pronounced stereoselectivity of the teratogenic, but not the anticonvulsant and sedative effect (Hauck et al., Life Sci. (1990) 46:513–518; Nau et al., Pharmacol. & Toxicol. (1991) 69:310–321. Carbon chains connected to carbon atom 2 of valproate which were shorter or longer than 3 carbons reduced teratogenic activity. Nau et al. Id. Valproate's antimitotic activity has been suggested as being related to its teratogenic potential rather than as a potential therapeutic asset, as the non-teratogenic valpromide analogue is not antiproliferative (Regan et al., Toxic in Vitro (1991) 5:77–82). Teratogenic analogs of valproate have been synthesized to date for the purpose of producing more desirable antiepileptic agents having fewer or no side effects and have not been suggested as being useful in their own right for other therapeutic purposes.

Despite continued efforts to identify compounds useful for treating neurodegenerative and proliferative disorders there is still a great need for useful compounds of increased efficacy and potency.

SUMMARY OF THE INVENTION

This invention provides compounds, pharmaceutical compositions and methods useful for promoting neuronal function and inhibiting cell mitosis. Accordingly, this invention also provides methods of preventing and treating neurodegenerative and proliferative disorders.

The compounds of this invention have the general formula (I)

(I)

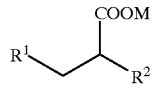

wherein $R^1$ is —C≡CH, —CH═$CH_2$ or —$CH_2$—$CH_3$, $R^2$ is a saturated, unsaturated, branched or unbranched $C_1$–$C_{30}$ alkyl group which is optionally substituted with a $C_3$–$C_9$ aliphatic or aromatic cyclohydrocarbon or heterocyclic group.

M is a hydrogen or a metal atom. Formula I is not 2-n-propyl-4-pentynoic acid (4-yn-VPA) or 2-n-propyl-4-pentenoic acid (4-en-VPA) and when $R_1$ is —$CH_2$—$CH_3$, $R^2$ is $C_5$ to $C_{30}$.

This invention also provides a method of making the compounds of the invention.

This invention also provides pharmaceutical compositions useful for inhibiting cell mitosis and/or promoting neuronal function comprising effective amounts of the compounds suitable for use in the treatments of the invention with a pharmaceutical carrier suitable for administration to an individual In addition, this invention relates to methods of promoting neuronal function and/or survival, and in particular to methods of treating individuals with neurodegenerative disorders. The compounds useful for treating neurodegenerative disorders include those of formula I as described above including 2-n-propyl-4-pentenoic acid and 2-n-propyl-4-pentynoic acid, as well as those of formula II (II)

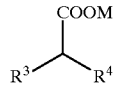

wherein $R^3$ and $R^4$ are independently of one another $C_1$–$C_{30}$ saturated or unsaturated, branched and/or unbranched aliphatic hydrocarbon, optionally substituted by a $C_{3-9}$ aliphatic or aromatic cyclohydrocarbon, or heterocyclic group. M is hydrogen or a metal atom.

The compounds and compositions of this invention which are neurotrophic may be used to promote the survival and function of neurons which would otherwise have diminished function, degenerate or die. Accordingly, in addition to treating individuals diagnosed with a neurodegenerative disorder, the compounds and compositions of this invention may also be used prophylactically to prevent or retard the onset of neurodegenerative disorders in individuals identified as being at risk for developing such disorders.

In another embodiment of this invention, the compounds and compositions useful for treating neurodegenerative disorders may also be used to treat proliferative disorders. The antiproliferative activity of the compounds and compositions may be used to prevent or retard the formation of a wide variety of tumors by administering the compounds and compositions to a person in need of treatment. This treatment is especially useful for treating tumors of neuronal or glial origin given that these compounds penetrate the CNS.

It is an object of this invention to provide neurotrophic compounds useful for enhancing the survival of neurons and glial cells.

It is another object of this invention to provide compound and compositions useful for promoting the expression of characteristics associated with mature functioning neuronal or glial cells.

By promoting the survival and function of neuronal or glial cells, it is an object to this invention to provide compounds and compositions useful for the prevention and/or treatment of a variety of neurodegenerative disorders.

Another object of this invention is to provide compounds and compositions useful for inhibiting the pathologic proliferation of neuronal, glial or related cells.

BRIEF DESCRIPTION OF THE [FIGURES] *DRAWINGS*

FIG. 1: Dose-Response relationship of antiproliferative effect of 2-n-butyl-4-pentynoic acid; and 2-n-pentyl-4-pentynoic acid. Neuro-2a neuroblastoma cells were cultured in 25 $cm^2$ flasks for 48 hours in the presence of test medium. After 48 hours, cells were observed, photographed and harvested with trypsin for counting using a haemocytometer. Cell number is expressed as percentage mean±SEM (n=3) of control values.

Figures 1, 3A:
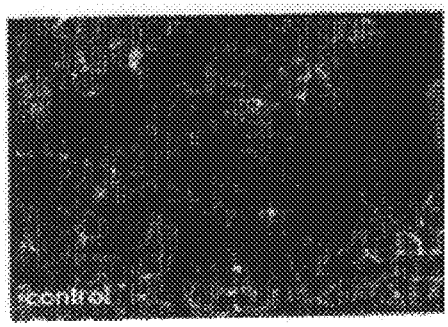
Figures 2, 3A:
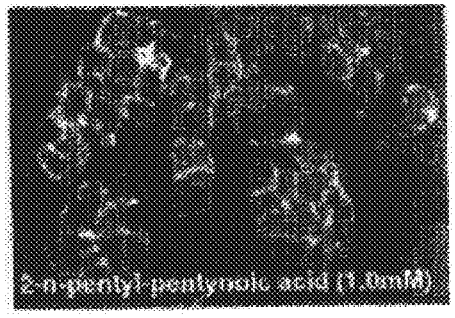

[FIG. 2: Induction of neurite outgrowth of neuro-2a neuroblastoma cells. Neuroblastoma cells were cultured in the presence of 2-n-butyl-4-pentynoic acid (1.0 mM, 2mM); and 2-n-pentyl-4-pentynoic acid (0.3 mM, 0.5 mM). Test medium was added to cells after 24 hours in culture and maintained as a test medium for 48 hours after which they were fixed in 2.5% glutaraldehyde and 0.5M sodium phosphate buffer overnight at 4° C. Cells were postfixed with osmium tetroxide and prepared for scanning microscopy as described. Fixed and stained cells were observed in a scanning electron microscope at an accelerating voltage of 15 kV.]

*FIGS. 2A–2E: Induction of neurite outgrowth of neuro-2a neuroblastoma cells. Neuroblastoma cells were cultured in the presence of 2-n-butyl-4-pentynoic acid (1.0 mM, 2 mM); and 2-n-pentyl-pentynoic acid (0.3 mM, 0.5 mM). Test medium was added to cells after 24 hours in culture and maintained as a test medium for 48 hours after which they were fixed in 2.5% glutaraldehyde and 0.5 M sodium phosphate buffer overnight at 4° C. Cells were postfixed with osmium tetroxide and prepared for scanning microscopy as described. Fixed and stained cells were observed in a scanning electron microscope at an accelerating voltage of 15 kV.*

Figure 3B:
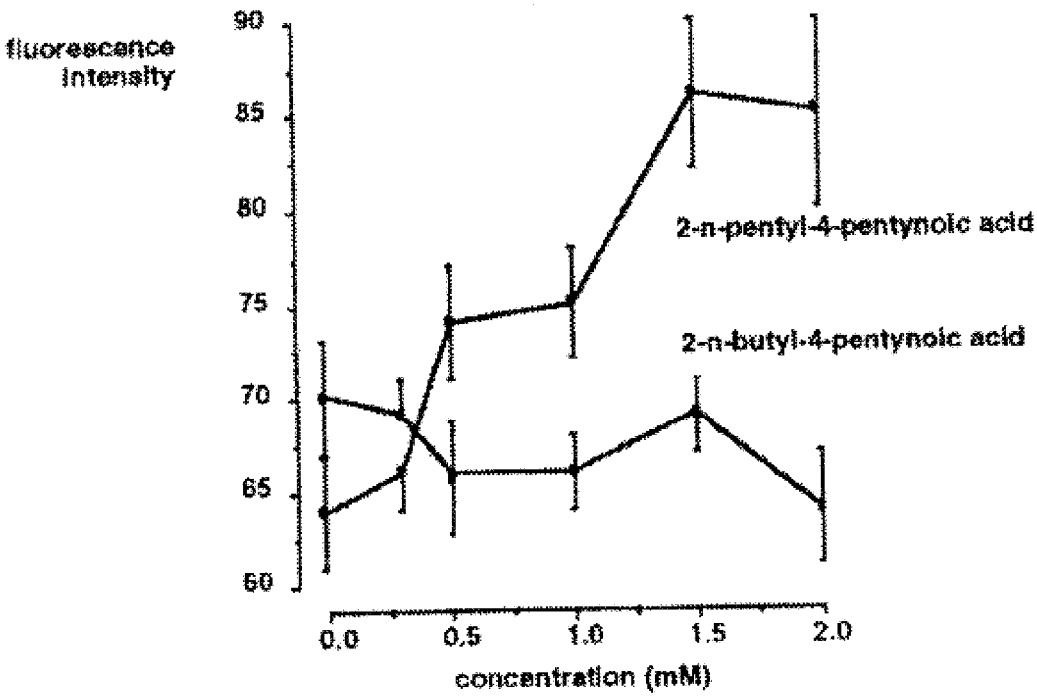

[FIG. 3: Neural Cell Adhesion Molecule (NCAM) immunofluorescence in neuro-2a neuroblastoma cells. Panel A. Cells gown in the presences of 2-n-pentyl-pentynoic acid (1.0 mm) show increased immunofluorescence directed against NCAM compared to control cells. Panel B. Neuroblastoma cells were cultured for 48 hours in the presence of increasing concentrations of 2-n-butyl-4-pentynoic acid and 2-n-pentyl-4-pentynoic acid. They were then fixed and prepared for staining with rabbit anti-NCAM antibody. A second anti-rabbit antibody conjugated to rhodamine was incubated with the cells to detect bound anti-NCAM antibody. Cells were observed with a fluorescence microscope at an excitation wavelength of 535 nm. Immunofluorescence is expressed as mean±SEM.]

*FIGS. 3A-1, 3A-2 and 3B: Neural Cell Adhesion Molecule (NCAM) immunofluorescence in neuro-2a neuroblastoma cells. Panel A. Cells grown in the presences of 2-n-pentynoic acid (1.0 mm) show increased immunofluorescence directed against NCAM compared to control cells. Panel B. Neuroblastoma cells were cultured for 48 hours in the presence of increasing concentrations of 2-n-butyl-4-pentynoic acid and 2-n-pentyl-4-pentynoic acid. They were then fixed and prepared for staining with rabbit anti-NCAM antibody. A second anti-rabbit antibody conjugated to rhodamine was incubated with the cells to detect bound anti-NCAM antibody. Cells were observed with a fluorescence microscope at an excitation wavelength of 535 nm. Immunofluorescence is expressed as mean +/– SEM.*

DETAILED DESCRIPTION OF THE INVENTION

This invention relates to derivatives of valproic acid, methods of their preparation and pharmaceutical compositions comprising these compounds. This invention also relates to a method of promoting neuronal function and differentiation which is useful for preventing and treating neurodegenerative disorders. The anti-mitotic activity of the compounds and compositions of the invention are useful for arresting cells in a specific stage of the cell cycle and for the prevention and treatment of neoplastic disease.

The objects of this invention are accomplished by providing potent teratogenic analogs of valproic acid which penetrate the CNS as neurotrophic/neuroprotective agents capable of treating and retarding the onset of neurodegenerative diseases. The compounds and compositions of this invention are also useful for controlling the cell proliferative rate and the metastatic potential of neoplastic or potentially neoplastic cells.

Accordingly, the compounds of this invention have the general formula (I)

(I)

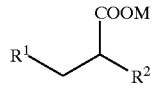

wherein $R^1$ is —C≡CH, —CH=$CH_2$, or —$CH_2$—$CH_3$, $R_2$ is independently a saturated, unsaturated with at least one double or triple bond, branched or unbranched $C_{1-30}$ alkyl group, optionally substituted with an aliphatic or aromatic $C_{3-9}$ cyclohydrocarbon or heterocyclic group; with the proviso that when $R^1$ is $CH_2$—$CH_3$, $R^2$ is $C_{5-30}$, and that formula I is not 2-n-propyl-4-pentynoic acid or 2-n-propyl-4-pentenoic acid (4-en-VPA).

M is a hydrogen or a metal atom.

This invention also includes the racemic mixtures and the separate enantiomeric R and S forms of the compounds and pharmaceutical acceptable salts thereof.

Preferably, $R^1$ is —C≡CH and $R^2$ is an unbranched saturated $C_2$–$C_{10}$ alkyl group. More preferred, $R^2$ is an unbranched, saturated $C_4$–$C_6$alkyl group. Examples of preferred substituents for $R^2$include —$(CH_2)_{1-9}$—$CH_3$, more preferred is —$(CH_2)_{3-6}$—$CH_3$, and most preferred is —$(CH_2)_{4-5}$—$CH_3$. Most preferred compounds are 2-n-butyl-4-pentynoic acid ($R^1$=—C≡H; $R^2$=—$(CH_2)_3$—$CH_3$)), 2-n-pentyl-4-pentynoic acid ($R^1$=—C≡H; $R^2$=—$(CH_2)_4$—$CH_3$) and 2-n-hexyl-4-pentynoic acid ($R^1$=—C≡H; $R^2$=—$(CH_2)_5$—$CH_3$). In addition, although both enantiomers and their racemic mixtures are considered within the scope of this invention, the S-enantiomeric form is preferred. Preferred metal atoms are sodium or other alkali metals, as well as alkaline earth metals such as, for example, calcium or magnesium.

The teratogenic, antiproliferative and prodifferentiative potencies of the preferred compounds are much higher than of the antiepileptic drug valproic acid.

Further branching of $R^1$ or $R^2$ reduces the potency of the corresponding compounds. This is demonstrated by the low teratogenic, antiproliferative and prodifferentiative potency of the following compound.

(III)

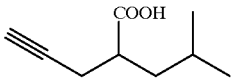

Unsaturation between $C_2$ and $C_3$ (IV) as well as methylation of the $C_5$ (V, VI) also lowers, but does not abolish, the above mentioned cellular neurotrophic and antiproliferative activity (IV)

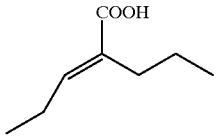

2-n-propyl-2-pentenoic acid (V)

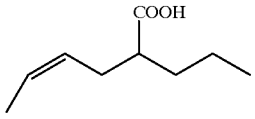

2-n-propyl-4-hexenoic acid (VI)

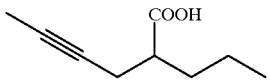

2n-propyl-4-hexynoic acid

In agreement with our basic hypothesis, compound IV (Nau et al., Neurology (1984) 34:400–402; Nau and Löscher, Fundam Appl. Toxicol. (1986) 6:669–676; Nau and Scott, Nature (1986) 323:276–278; Vorhees et al., Teratology (1991) 43:583–590; Ehlers et al., Devel. Pharmacol. Ther. (1992) 19:196–204 and VI (Nau et al., Pharmacol. & Toxicol. (1991) 69:310–321; Elmazar et al., J. Pharm. Sci. (1993) 82:1255–1258 has very low or undetectable teratogenic activities, but good anticonvulsant properties in experimental models.

The compounds and compositions of this invention are more potent teratogenic analogues of valproate and exhibit greater antiproliferative and neurotrophic/neuroprotective activity than the parent. In contrast to saturated valproate analogues (where both chains must contain 3 carbon atoms each for maximal activity) a double or triple bond in the ω position of one chain exhibits higher activities when the other chain contains 4 to 6 carbon atoms. The 2-n-propyl-4-pentynoic acid, 2-n-butyl-4-pentynoic acid, 2-n-pentyl-4-pentynoic acid and 2-n-hexyl-4-pentynoic acid are the most potent valproate-related teratogens synthesized. 2-n-butyl-4-pentynoic acid, 2-n-pentyl-4-pentynoic and 2-n-hexyl-4-pentynoic acid are more preferred. Most preferred are 2-n-pentyl-4-pentynoic acid and 2-n-hexyl-4-pentynoic acid.

The preferred compounds for use with this invention possess a chiral alpha-carbon. As a result of chirality, the efficacy and potency of different enantiomeric forms may differ. For example, S-2-n-propyl-4-pentynoic acid has significantly greater teratogenic potential than the R-enantiomeric form. Hauck and Nau, Pharm. Res. (1992) 9:850–855; Hauck et al. Toxicol. Lett. (1992) 60:145–153. See Nau et al. Pharmacol. Toxicology (1991) 69:310–321 which is incorporated herein by reference. Although there is no general rule of the above-identified compounds, the S enantiomeric form is preferred.

The compounds of this invention are prepared by reacting an appropriately substituted malonic acid diethylester with an appropriate unsaturated alkylating agent such as a straight-chain alkylhalide. The product is then hydrolyzed and decarboxylated.

The reaction can also be carried out in the reciprocal manner in that a malonic acid diethylester, substituted with an unsaturated function is reacted with an appropriate alkylhalide. This reaction is again followed by hydrolysis and decarboxylation.

The novel compounds of this invention may be produced according to the method of this invention. In one embodiment, the method of synthesizing the compounds comprises combining a malonic acid diester reactant with a first halide reactant having the general formula $$R^2—X \qquad \text{(VII)}$$

wherein $R^2$ is a saturated or unsaturated branched or unbranched $C_1$–$C_{30}$ alkyl group and X is a halide. This first reaction produces a 2-alkyl-malonic acid diester. The 2-alkyl-malonic acid diester is then further combined with a second halide reactant having the general formula $$R^1—CH_2—X \qquad \text{(VIII)}$$

wherein $R^1$ is —C≡CH, —CH=$CH_2$or —$CH_2$—$CH_3$ to produce compounds with the general formula (IX)

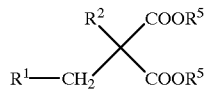

wherein $R^5$ is an alkyl group.

The resulting diesters are then hydrolyzed, decarboxylated and optionally converted into a salt.

In an alternative embodiment, the order of carrying out the reactions is reversed, such that the $R^1$—$CH_2$—X is combined with the malonic acid diester followed by further reaction with the $R^2$—X.

In a preferred method of preparing the compounds of this invention, malonic acid diethylester is treated with a base, for example, sodium ethylate, to deprotonate carbon 2. Subsequent treatment of the resulting deprotonated ester with an alkylating agent in the form of a straight-chain alkyl halide yields a 2-n-alkyl-malonic acid diethylester.

(X)

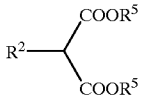

This product is further alkylated with sodium ethylate and either 2-propynehalide to yield XI (XI)

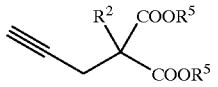

or 2-propenehalide to yield XII (XII)

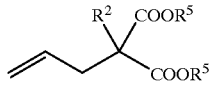

or 2-propylhalide to yield XIII (XIII)

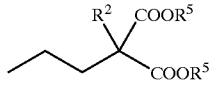

The diesters (XI) and (XII) and (XIII) are hydrolyzed and decarboxylated with potassium hydroxide in ethanol/water with heat treatment.

Another embodiment of this invention is the promotion of neural function by contacting neural cells with a neurotrophic amount of a compound of formula (II)

(II)

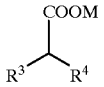

wherein $R^3$ and $R^4$ are independently of each other saturated or unsaturated, branched, or unbranched, $C_1$–$C_{30}$ aliphatic hydrocarbons, optionally possessing at least one double or triple bond. Preferably $R^3$ and $R^4$ are unbranched, and $R^3$ is less than or equal to a three carbon chain. $R^4$ preferably is a saturated alkyl group and is preferably from $C_2$–$C_{10}$, as in for example —$(CH_2)_{1-9}$—$CH_3$, and more preferably from $C_4$ to $C_6$, as in for example —$(CH_2)_{3-5}$—$CH_3$. In addition to the compounds stated above in connection with formula I, other compounds which are useful for the promotion of neuronal function and inhibition of cell mitosis are described in Nau et al. PCT application PCT/DE93/00861 publish as WO94/06743, and which is incorporated herein by reference.

Preferred compounds useful for promoting neuronal function include for example, 2-n-propyl-4-pentynoic acid ($R^3$=—$CH_2$—C≡CH; $R^4$=—$(CH_2)_2$—$CH_3$); valproic acid ($R^3$=$R^4$=—$(CH_2)_2$—$CH_3$); 2-n-propylhexanoic acid ($R^3$=—$(CH_2)_3$—$CH_3$, $R^4$=—$(CH_2)_2$—$CH_3$); and 2-n-butylhexanoic acid ($R^3$=—$(CH_2)_3$—$CH_3$).

The promotion of neuronal function is particularly useful for preventing and treating neurodegenerative disorders. Neurodegenerative disorders include any disorder resulting in neuronal degeneration which is responsive to at least one of the valproate analogues or valproate itself.

The neurotrophic activity associated with valproate and its analogues may be determined based on in vitro indices of differentiation, including inhibition of mitosis, increase in neurite outgrowth, and NCAM expression. For example, the ability to promote neurite outgrowth is correlated with enhanced survival of certain cultured neural cells including embryonic sensory and sympathetic neurons. Proliferating immature neuroblasts, in vitro, have a rounded shape and are loosely adherent to culture surfaces. In the presence of a neurotrophic factor, these cells become more adherent and sprout processes known in the art as neurites. Accordingly, in vitro neurite outgrowth may be used as an assay for determining concentrations of compound in contact with target cells which would be expected to achieve desirable neuroprotecting effects.

Methods of assessing neurite outgrowth in vitro are well known in the art and, for example, may be assessed through direct microscopic visual inspection or through the use of computer aided image processing.

Another characteristic of neurotrophic factors which may be used to assess the neuroprotective action of the compounds and compositions of this invention is their ability to promote survival or certain specific cell types. For example, NGF is required in vitro for the survival of certain specific cell types which die in the absence of NGF. Such NGF dependent cells include neurons of the chick dorsal rat ganglia at about embryonic day E5to E8.

Scanning electron microscopy illustrates the cells ability to increase cell-substratum adhesivity. They eliminate rounded and clustered growth, typical of tumor cells, and induce a flattening and greater interaction with the substratum (FIG. 2). In vivo, it is generally believed that these neurites further differentiate into axons and dendrites and form synapses with other neurons. During diseases involving neurodegeneration, there may be a loss of synapses and degeneration of axons and dendrites resulting in a deficit of neuronal function.

Another index of differentiation resulting from the neurotrophic activity of valproate analogues is an increase in NCAM expression. Further, increases in NCAM prevalence enhances neurite outgrowth. Doherty et al., Nature (1990) 343:464–466. NCAM has been reported as playing a fundamental role in memory formation as intraventricular infusion of anti-NCAM during consolidation of a recent learning event induces an amnesia. Doyle et al., J. Neurochem. (1992) 59:1570–1573, which is incorporated herein by reference. Rapid endocytosis of the Aplysia NCAM homologue was reported following a serotonin-induced change in synapse structure in vitro. Bailey et al., Science (1992) 256:645–649.

During development of individual brain regions, or in adults exhibiting ongoing neurogenesis, NCAM transiently increases its sialylation state. See review, Regan, Int. J. Biochem. (1991) 23:513–523, which is incorporated herein by reference, Rougon (1993) Eur. J. Cell Biol. 61:197–207. The synapse specific NCAM isoform (NCAM 180) which is associated with differentiated neurons increases its sialylation state during later stages of development until the period of synaptogenesis is complete. Breen et al., J. Neurochem (1988) 50:712–716. A similar isoform-specific sialylation of NCAM 180 occurs during consolidation of a passive-avoidance response. Doyle et al., J. Neurosci Res., (1992) 31:513–523.

Accordingly, the methods of treatment and prevention of neurodegenerative diseases rely on the ability of valproate and its analogues to possess neurotrophic activity such as promoting neurite outgrowth and survival of neuronal cells and NCAM expression.

It is contemplated that the methods of treatment may provide benefits to persons with neurodegeneration from disorders including, but not limited to ALS, Alzheimers disease, Parkinson's disease, Huntington's disease, diabetic neuropathy and stroke. In addition, the neurite promoting activity of the disclosed compounds and compositions would also provide benefits to individuals with traumatic nerve injury.

IN another embodiment of this invention, methods are provided for arresting cells in a specific stage of the cell cycle which leaves the cells in a differentiated state by contacting cells with a mitotic inhibitory amount of a compound of formula II as described above. Preferred substituents for $R^3$, $R^4$ and M for inhibiting mitosis are the same as those for promoting neuronal function, with the proviso that formula II is not valproate if simply used to inhibit cell mitosis. Preventing mitosis in this manner is useful for enhancing the expression of specific proteins associated with the differentiated phenotype. This enhanced expression facilitates purification of such proteins. In addition, arresting or retarding mitosis is useful for treating proliferative disorders by administering to individuals in need of treatment valproate and/or another of its anti-mitotic analogues.

We have observed sensitivity to valproate or its antimitotic analogues in all cells tested. Such cell types include: primary astrocytes, human astrocytoma, and those from cardiac, renal, and immune systems. Accordingly, the antiproliferative action of valproate and its other analogues described herein should have broad applicability for a wide variety of tumors derived from a variety of cell types and particularly those mentioned above.

The neurotrophic and/or anti-mitotic effective amounts of valproate and active analogues may be determined using standard dose-response curves. Accordingly, representative cells may be cultured in vitro in the presence of varying concentration of test compound. At an appropriate time, the cells under the different conditions are examined for the appropriate parameter (for example, cell number for antimitotic activity; neurite outgrowth for neurotrophic activity) and the $ED_{50}$ may be determined.

The preferred compounds of this invention exert a most profound antiproliferative action with ED50 values well below (<0.5 mM) those observed with valproate (FIG. 1). Thus, these compounds may be expected to act an concentrations which will be devoid of the sedative and hepatotoxic side effects of valproate. The preferred compounds also exert the prodifferentiative action observed with valproate. In the neuro-2a neuroblastoma cell line they induce a marked neuritogenic response which correlates with their antiproliferative potential (FIG. 2).

In addition, the more potent of these compounds increase neural cell adhesion molecule (NCAM) prevalence (FIG. 3). This cell recognition system regulates neural plasticity during development and, later, during information storage in the adult animal by altering its prevalence and glycosylation state (Doyle et al., J. Neurosci Res., (1992) 31:513–523). Drugs which reverse scopolamine-induced amnesia, such as piracetam-related compounds, appear to act through a neuroprotective mechanism which involves a non-specific increase in NCAM glycosylation and/or prevalence (Doyle et al., J. Neurochem. (1993) 61:266–272). Consequently agents which would induce NCAM expression may be predicted to have neuroprotective potential.

This invention also provides pharmaceutical compositions useful for treating neurodegenerative or proliferative disorders comprising a compound selected from formulas I or II as described above. In addition to the compounds of formula I or II, the pharmaceutical composition may also comprise adjuvant substances and carriers. The compositions may be in the form of tablets, capsules, powders, granules, lozenges, suppositories, reconstitutable powders, or liquid preparations such as oral or sterile parenteral solutions or suspensions.

In order to obtain consistency or administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone, fillers, for example lactose, sugar, maize-starch, calcium phosphate, sorbitol or glycine; disintegrants, for example starch, polyvinylpyrrolidone, sodium starch glycolate or microcrystalline cellulose; or pharmaceutically acceptable wetting agents such as sodium lauryl sulphate.

The solid oral compositions may be prepared by conventional methods of blending, filling, tabletting or the like. Repeated blending operation may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; nonaqueous vehicles (which may include edible oils), for example almond oil fractionated coconut oil, oily esters such as esters of glycerine, propylene glycol, or ethyl alcohol; preservatives, for example methyl or propyl p-hydroxybenzoate of sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared is substantially the same manner, except that the compound is suspended in the vehicle instead or being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The dose of the compound used in the treatment of such disease will vary in the usual way with the seriousness of the disorders, the weight of the sufferer, and the relative efficacy of the compound.

Antiproliferative and neuroprotective actions should be sufficient to achieve the desired inhibition of mitosis or neuroprotection without serious hetaptotoxic side effects. The plasma concentrations to be achieved will be sufficient to provide therapeutically effective concentrations of compound in contact with the target cells. Standard clinical techniques may be used to determine the effective amount of compound to be administered to achieve the desired therapeutic effect. Dose response curves may be determined first in vitro in a relevant animal model to determine ranges of expected therapeutic concentrations in humans. For example, mitosis of mouse neuro-2a-neuroblastoma cells is inhibited by valproate with an $ED_{50}$ of 1.0–1.3 mM. Other cell lines, including those of human origin may be used to assesses activity as well.

EXAMPLE 1

0.1 mol n-butyl malonic acid diethylester and 0.1 mol 3-bromo-1-propine were placed in a dry argon flushed flask and heated to 60° C. To this mixture was added 0.1 mol sodium ethanolat (prepared from 0.1 mol sodium and 50 mol dry ethanol) dropwise such as to keep the mixture boiling. After completion of the addition, the mixture was heated until TLC (Silica alu sheets, hexane/ethylacetate 7.5/1) showed absence of starting material (usually 1–2 hours). The ethanol was evaporated under reduced pressure, the remaining salts were dissolved in water and the product was extracted three times with $CH_2Cl_2$. The organic phase was dried over sodium sulfate and evaporated The distillation under reduced pressure resulted in the unsymmetrically substituted malonic acid diethylester.

$bP_{0.3}$ mbar:78°–82° C.

The dialkylated malonic esters were heated in a solution of 20.3 g (0.35 mol) potassium hydroxide, 50 ml water and 100 ml ethanol. After completion of the saponification, ethanol was evaporated under reduced pressure. The remaining residue was diluted with water and washed with ether. The water layer was acidified with concentrated HCl (pH<2) and extracted with ether. Drying over anhydrous sodium sulfate and concentration under reduced pressure yielded crude dialkyl malonic acid. Decarboxylation was achieved by heating of the crude product (120°–180° C.). The dark residue was distilled twice in vacuo resulted in the desired products.

Overall yield: 18%

$bP_{0.1}$ mbar: 75°–78° C.

$1_{H\text{-}NMR}$ ($CDCl_3$): 0.94 (3H, t, $CH_3$), 1.34 (4H, m, 2×$CH_2$), 1.72 (2H, m, $CH_2$—CHRCOOH), 2.04 (1H, t, C≡C—H), 2.36–2.68 (3H, m, CHRCOOH—$CH_2$—C≡C), 11.88 (1H, s, broad, COOH)

EXAMPLE 2

0.1 mol n-pentyl malonic acid diethylester is reacted with 0.1 mol 3-bromo-1-propine as described in example 1.

Overall yield: 14%

$bP_{15}$ mbar: 135° C.

$1_{H\text{-}NMR}$ ($CDCL_3$): 0.92 (3H, t, $CH_3$), 1.32 (6H, m, 3=$CH_2$), 1.72 (2H, m, $CH_2$—CHRCOOH), 2.04 (1H, t, C≡C—H), 2.40–2.72 (3H, m, CHRCOOH—$CH_2$—C≡C), 11.32 (1H, s, broad, COOH)

EXAMPLE 3

(±)-2-(2-propinyl)-Octanoic acid (Hexyl-4-yn)

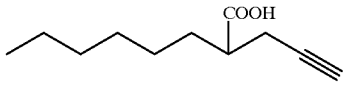

Synthesis is by the dianion method (Petragnani, Synthesis 521, 1982).

All glassware was oven dried and the reaction apparatus was flushed with argon throughout the entire operation.

Lithium-dianion (0.2 Mol) was prepared by adding 0.2 Mol n-butyl-lithium to a solution of 0.2 Mol freshly distilled diisopropylamine and 130 ml dry tetrahydrofurane at 0° C. Octanoic acid (0.1 Mol) was added followed by 19 hexamethylphosphoric acid triamide to effect solution of the dianion. The resulting mixture was stirred at room temperature for 30 min followed by cooling to −60° C. and addition of 3-bromo-1-propin (0.1 Mol) quickly via a syringe. The temperature rose instantly. After cooling back to −60° C., the reaction was stirred and monitored by TLC (Hexane:Ethylacetate=7.5:1 plus 5% acetic acid) until completion (ca 1.5 h). Cooling was removed and 200 ml 10% HCl was added. The phases were separated and the water phase was extracted twice with ether. The combined organic phases were washed with half saturated NaCl solution and dried with $Na_2SO_4$. Evaporation of the solvent yielded a yellow oil. Destillation yielded a colorless liquid (bp. 82°–84° C., 0.1 mbar). $^1H$ NMR ($CDCl_3$)=0.88 (3H, t, $CH_3$), 1.40 (8H, mc, $CH_2$), 1.90 (2H, mc, $CH_2$), 2.04 (1H, t, ≡—H), 2.32–2.68 (3H, m, $CH_2$, $H_\alpha$), 12.04 (1H, s broad, COOH).

EXAMPLE 4

The following non-limiting preferred examples are compounds within the scope of this invention:

2-n-propyl-4-pentynoic acid
2-n-prop-$1^1$-enyl-4-pentynoic acid
2-n-prop-$2^1$-enyl-4-pentynoic acid
2-i-propyl-4-pentynoic acid
2-i-propenyl-4-pentynoic acid
2-n-butyl-4-pentynoic acid
2-n-but-$1^1$-enyl-4-pentynoic acid
2-n-but-$2^1$-enyl-4-pentynoic acid
2-n-but-$3^1$-enyl-4-pentynoic acid
2-($1^1$-methylbutyl)-4-pentynoic acid
2-($1^1$-methylprop-$1^1$-enyl)-4-pentynoic acid
2-($1^1$-methylprop-$2^1$-enyl)-4-pentynoic acid
2-($2^1$-methylpropyl)-4-pentynoic acid
2-($2^1$-methylprop-$1^1$-enyl)-4-pentynoic acid
2-($2^1$-methylprop-$2^1$-enyl)-4-pentynoic acid
2-tert.-butyl-4-pentynoic acid
2-n-pentyl-4-pentynoic acid
2-($1^1$-methylbutyl)-4-pentynoic acid
2-($2^1$-methylbutyl)-4-pentynoic acid
2-($3^1$-methylbutyl)-4-pentynoic acid
2-($1^1$,$1^1$-dimethylpropyl)-4-pentynoic acid
2-($1^1$,$2^1$-dimethylpropyl)-4-pentynoic acid
2-($2^1$,$2^1$-dimethylpropyl)-4-pentynoic acid
2-n-hexyl-4-pentynoic acid
2-n-hex-$1^1$-enyl-4-pentynoic acid
2-n-hex-$2^1$-enyl-4-pentynoic acid
2-n-hex-$3^1$-enyl-4-pentynoic acid
2-n-hex-$4^1$-enyl-4-pentynoic acid
2-n-hex-$5^1$-enyl-4-pentynoic acid
2-($1^1$-methylpentyl)-4-pentynoic acid 2-($1^1$-methylpent-$1^1$-enyl)-4-pentynoic acid
2-($1^1$-methylpent-$2^1$-enyl)-4-pentynoic acid
2-($1^1$-methylpent-$3^1$-enyl)-4-pentynoic acid
2-($1^1$-methylpent-$4^1$-enyl)-4-pentynoic acid
2-($2^1$-methylpentyl)-4-pentynoic acid
2-($2^1$-methylpent-$1^1$-enyl)-4-pentynoic acid
2-($2^1$-methylpent-$2^1$-enyl)-4-pentynoic acid
2-($2^1$-methylpent-$3^1$-enyl)-4-pentynoic acid
2-($2^1$-methylpent-$4^1$-enyl)-4-pentynoic acid
2-($3^1$-methylpentyl)-4-pentynoic acid
2-($3^1$-methylpent-$1^1$-enyl)-4-pentynoic acid
2-($3^1$-methylpent-$2^1$-enyl)-4-pentynoic acid
2-($3^1$-methylpent-$3^1$-enyl)-4-pentynoic acid
2-($3^1$-methylpent-$4^1$-enyl)-4-pentynoic acid
2-($4^1$-methylpentyl)-4-pentynoic acid
2-($4^1$-methylpent-$1^1$-enyl)-4-pentynoic acid
2-($4^1$-methylpent-$2^1$-enyl)-4-pentynoic acid
2-($4^1$-methylpent-$3^1$-enyl)-4-pentynoic acid
2-($4^1$-methylpent-$4^1$-enyl)-4-pentynoic acid
2-($1^1$,$1^1$-dimethylbutyl)-4-pentynoic acid
2-($1^1$,$1^1$-dimethylbut-$2^1$-enyl)-4-pentynoic acid
2-($1^1$,$1^1$-dimethylbut-$3^1$-enyl)-4-pentynoic acid
2-($1^1$,$2^1$-dimethylbutyl)-4-pentynoic acid
2-($1^1$,$2^1$-dimethylbut-$1^1$-enyl)-4-pentynoic acid
2-($1^1$,$2^1$, dimethylbut-$2^1$-enyl)-4-pentynoic acid
2-($1^1$,$2^1$, dimethylbut-$3^1$-enyl)-4-pentynoic acid
2-($1^1$,$3^1$-dimethylbutyl)-4-pentynoic acid
2-($1^1$,$3^1$-dimethylbut-$1^1$-enyl)-4-pentynoic acid
2-($1^1$,$3^1$-dimethylbut-$2^1$-enyl)-4-pentynoic acid
2-($1^1$,$3^1$-dimethylbut-$3^1$-enyl)-4-pentynoic acid
2-($2^1$,$2^1$-dimethylbutyl)-4-pentynoic acid
2-($2^1$,$2^1$-dimethylbut-$3^1$-enyl)-4-pentynoic acid
2-($2^1$,$3^1$-dimethylbutyl)-4-pentynoic acid
2-($2^1$,$3^1$-dimethylbut-$1^1$-enyl)-4-pentynoic acid
2-($2^1$,$3^1$-dimethylbut-$2^1$-enyl)-4-pentynoic acid
2-($2^1$,$3^1$-dimethylbut-$3^1$-enyl)-4-pentynoic acid
2-($3^1$,$3^1$-dimethylbutyl)-4-pentynoic acid
2-($3^1$,$3^1$-dimethylbut-$1^1$-enyl)-4--pentynoic acid
2-($1^1$,$1^1$,$2^1$-trimethylpropyl)-4-pentynoic acid
2-($1^1$,$1^1$,$2^1$-trimethylprop-$2^1$-enyl)-4-pentynoic acid
2-($1^1$,$2^1$, $2^1$-trimethylpropyl)-4-pentynoic acid
2-n-heptyl-4-pentynoic acid
2-($1^1$-methylhexyl)-4-pentynoic acid
2-($2^1$-methylhexyl)-4-pentynoic acid
2-($3^1$-methylhexyl)-4-pentynoic acid
2-($4^1$-methylhexyl)-4-pentynoic acid
2-($5^1$-methylhexyl)-4-pentynoic acid
2-($1^1$,$1^1$-dimethylpentyl)-4-pentynoic acid
2-($1^1$,$2^1$-dimethylpentyl)-4-pentynoic acid
2-($1^1$,$3^1$-dimethylpentyl)-4-pentynoic acid
2-($1^1$,$4^1$-dimethylpentyl)-4-pentynoic acid
2-($2^1$,$2^1$-dimethylpentyl)-4-pentynoic acid
2-($2^1$,$3^1$-dimethylpentyl)-4-pentynoic acid
2-($2^1$,$4^1$-dimethylpentyl)-4-pentynoic acid
2-($3^1$,$3^1$-dimethylpentyl)-4-pentynoic acid
2-($3^1$,$4^1$-dimethylpentyl)-4-pentynoic acid
2-($4^1$,$4^1$-dimethylpentyl)-4-pentynoic acid
2-($1^1$,$1^1$,$2^1$-trimethylbutyl)-4-pentynoic acid
2-($1^1$,$1^1$,$3^1$-trimethylbutyl)-4-pentynoic acid
2-($1^1$,$2^1$,$3^1$-trimethylbutyl)-4-pentynoic acid
2-($2^1$,$2^1$,$3^1$-trimethylbutyl)-4-pentynoic acid
2-($2^1$,$3^1$,$3^1$-trimethylbutyl)-4-pentynoic acid

EXAMPLE 5

Maintenance of Cell Lines.

The mouse neuro-2a neuroblastoma cell line (Klebe and Ruddle, 1969 J. Cell Biol., 43:69A) was cultured in Dulbecco's modified Eagle's medium (DMEM; Flow Laboratories) supplemented with 10% fetal bovine serum (Tissue Culture Services), 200 mM glutamine and 100 $\mu$g/ml of gentamicin or 100 units/ml and 100 $\mu$g/ml of penicillin/streptomycin antibiotics (Sigma Chemicals). The cells were maintained in a water-humidified atmosphere of 9% $CO_2$at 37° C. Cells were passaged using 0.025% trypsin (Gibco) in DMEM, and were seeded at a density of $1\times10^4$ cells/cm$^2$.

Antiproliferative Assay.

Neuro-2a cells were seeded in 25cm$^2$ flasks (Costar) at a density of $1\times10^4$ cells/cm$^2$. Following a recovery period of 24 h, the agent to be examined was added to the cells in a vehicle of dimethyl sulphoxide (DMSO), the volume of which was 0.2% of the total volume of medium bathing the cells. A flask containing the DMSO vehicle alone was employed as control. Following incubation for 48h, cells were examined using an inverted phase contrast microscope (Leitz Diavert) and photographed (Ilford 50ASA film). Cells were then harvested by trypsinization and were counted using a haemocytometer (improved Neubauer model). FIG. 1 shows the resultant decrease in cell proliferation.

Scanning Electron Microscopy.

Cells which were to be examined by scanning electron microscopy were grown as previously described in 25cm$^2$ flasks. Following 48 h exposure to the agent, cells were fixed in a solution of 2.5% glutaraldehyde in 0.1M sodium phosphate buffer, pH 7.4, overnight at 4° C. The cells were post-fixed subsequently in phosphate-buffered 1% osmium tetroxide for 1 h at room temperature, washed and were dehydrated gradually for 1 hour using a series of ethanol concentrations stepwise from 20, 40, 60, 80 to a final concentration 100%.

Sections of the base of the tissue culture flask were removed and were critical point dried to minimize shrinkage and cracking. This was achieved by placing the samples in a Polaron critical point dryer and purging the chamber several times with $CO_2$ to remove all traces of ethanol. After 1 h the temperature and pressure were increased to 40° C. and 1200 lbs/in$^2$, respectively, at which stage the critical point for carbon dioxide had been reached and drying was completed.

Specimens were subsequently removed from the chamber, mounted on stubs suitable for scanning electron microscopy using conductive carbon cement (Neubauer) and were sputter coated with gold under vacuum ($5\times10^{-2}$ torr) in the presence of argon gas at a current of 20 mA for 3 minutes (Polaron E5100). Following gold-coating, samples were examined in the scanning electron microscope (JEOL 35C) at an accelerating voltage of 15 kV. Images were recorded on film (Kodak Plus-X Pan 120 film) as shown in FIG. 2.

Fluorescence Microscopy.

Cells were seeded in 24-well plates at a density of $1\times10^4$ cells/cm$^2$. Following a recovery period 24 h they were exposed for an additional 48 h to the drug under investigation. Cells were progressively fixed by six ten-minute incubations with DMEM containing increasing concentrations of neutral buffered formalin stepwise from 10, 30, 50, 70, 90 to a final concentration of 100%. When fixation was complete, cells were washed three times with phosphate buffered saline pH 7.4 over a 30 minute period. The cells were then incubated with a 1 in 50 dilution of rabbit anti-NCAM antibody, (Pliophys et al. J. Neuropsychiatr. 2:413–417, 1990) in phosphate buffered saline containing 1% (W/V) bovine serum albumin for 1 h at RT and washed three times with phosphate buffered saline, pH 7.4 for 30 minutes. Washed cells were then incubated for 1 h at RT with the secondary anti-rabbit antibody diluted 1 in 50 in phosphate buffered saline containing 1% (W/V) bovine serum albumin (Sigma) which was conjugated to rhodamine. The cells were again washed three times with phosphate buffered saline pH 7.4 and were then mounted using Citifluor (Agar Scientific) containing a fluorescence enhancer. Fluorescence of rhodamine was visualized using an excitatory wavelength of 535 nm (Leica filter block N2.1) on a Leitz DMRB fluorescence microscope. Fluorescence intensity was examined at points of cell-cell contact using a Quantimet 500 Image Analysis System. Fluorescence intensity is expressed as grey level at points of cell contact relative to that observed in the control. FIG. 3 shows the increase in NCAM immunofluorescence.

While we have hereinbefore described a number of embodiments of this invention, it is apparent that the basic constructions can be altered to provide other embodiments which utilize the methods of this invention. Therefore, it will be appreciated that the scope of this invention is defined by the claims appended hereto rather than by the specific embodiments which have been presented hereinbefore by way of example.

We claim:

[1. Compounds of formula (I)

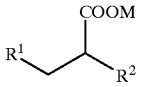

wherein $R^1$ is —C≡CH, —CH═$CH_2$, or —$CH_2$—$CH_3$, $R^2$ is a saturated, unsaturated, branched and/or unbranched $C_1$–$C_{30}$ alkyl group, optionally further comprising an aliphatic or aromatic $C_{3-9}$ cyclohydrocarbon or heterocyclic group comprising 3 to 9 atoms; and M is a hydrogen or a metal atom, and enantiomeres thereof and pharmaceutical acceptable salts thereof; with the proviso that the compound of formula (I) is not 2-n-propyl-4-pentynoic acid, 2-benzylpentanoic acid, 4,4'-dien-valproic acid or 2-n-propyl-4-pentenoic acid (4-en-VPA), and when $R^1$ is —$CH_2$—$CH_3$, $R^2$ is $C_5$ to $C_{30}$.]

[2. The compounds according to claim 1 wherein $R^1$ is —C≡CH or —CH═$CH_2$ and $R^2$ is unbranched and —$(CH_2)_{1-9}$—$CH_3$.]

[3. The compound according to claim 2 wherein $R^2$ is —$(CH_2)_{3-6}$—$CH_3$.]

[4. The compounds according to claim 2 wherein $R^2$ is —$(CH_2)_{4-5}$—$CH_3$.]

[5. The compounds according to claim 4 wherein $R^1$ is —C≡CH.]

[6. The S enantiomer of the compounds according to claim 1.]

[7. The compounds according to claim 1, selected from the group consisting of:

2-n-prop-$1^1$-enyl-4-pentynoic acid
2-n-prop-$2^1$-enyl-4-pentynoic acid
2-i-propyl-4-pentynoic acid
2-i-propenyl-4-pentynoic acid
2-n-but-$1^1$-enyl-4-pentynoic acid
2-n-but-$2^1$-enyl-4-pentynoic acid
2-n-but-$3^1$-enyl-4-pentynoic acid
2-($1^1$-methylbutyl)-4-pentynoic acid
2-($1^1$-methylprop-$1^1$-enyl)-4-pentynoic acid
2-($1^1$-methylprop-$2^1$-enyl)-4-pentynoic acid
2-($2^1$-methylpropyl)-4-pentynoic acid
2-($2^1$-methylprop-$1^1$-enyl)-4-pentynoic acid
2-($2^1$-methylprop-$2^1$-enyl)-4-pentynoic acid
2-tert.-butyl-4-pentynoic acid
2-n-pentyl-4-pentynoic acid
2-($1^1$-methylbutyl)-4-pentynoic acid
2-($2^1$-methylbutyl)-4-pentynoic acid
2-($3^1$-methylbutyl)-4-pentynoic acid
2-($3^1$-dimethylpropyl)-4-pentynoic acid
2-($1^1$,$1^1$-dimethylpropyl)-4-pentynoic acid
2-($2^1$,$2^1$-dimethylpropyl)-4-pentynoic acid
2-n-hexyl-4-pentynoic acid
2-n-hex-$1^1$-enyl-4-pentynoic acid
2-n-hex-$2^1$-enyl-4-pentynoic acid
2-n-hex-$3^1$-enyl-4-pentynoic acid
2-n-hex-$4^1$-enyl-4-pentynoic acid
2-n-hex-$5^1$-enyl-4-pentynoic acid
2-($1^1$-methylpentyl)-4-pentynoic acid
2-($1^1$-methylpent-$1^1$-enyl)-4-pentynoic acid
2-($1^1$-methylpent-$2^1$-enyl)-4-pentynoic acid
2-($1^1$-methylpent-$3^1$-enyl)-4-pentynoic acid
2-($1^1$-methylpent-$4^1$-enyl)-4-pentynoic acid
2-($2^1$-methylpentyl)-4-pentynoic acid
2-($2^1$-methylpent-$1^1$-enyl)-4-pentynoic acid
2-($2^1$-methylpent-$2^1$-enyl)-4-pentynoic acid
2-($2^1$-methylpent-$3^1$-enyl)-4-pentynoic acid
2-($2^1$-methylpent-$4^1$-enyl)-4-pentynoic acid
2-($3^1$-methylpentyl)-4-pentynoic acid
2-($3^1$-methylpent-$1^1$-enyl)-4-pentynoic acid
2-($3^1$-methylpent-$2^1$-enyl)-4-pentynoic acid
2-($3^1$-methylpent-$3^1$-enyl)-4-pentynoic acid
2-($3^1$-methylpent-$4^1$-enyl)-4-pentynoic acid
2-($4^1$-methylpentyl)-4-pentynoic acid
2-($4^1$-methylpent-$1^1$-enyl)-4-pentynoic acid
2-($4^1$-methylpent-$2^1$-enyl)-4-pentynoic acid
2-($4^1$-methylpent-$3^1$-enyl)-4-pentynoic acid
2-($4^1$-methylpent-$4^1$-enyl)-4-pentynoic acid
2-($1^1$,$1^1$-dimethylbutyl)-4-pentynoic acid
2-($1^1$,$1^1$-dimethylbut-$2^1$-enyl)-4-pentynoic acid
2-($1^1$,$1^1$-dimethylbut-$3^1$-enyl)-4-pentynoic acid
2-($1^1$,$2^1$-dimethylbutyl)-4-pentynoic acid
2-($1^1$,$2^1$-dimethylbut-$1^1$-enyl)-4-pentynoic acid
2-($1^1$,$2^1$,dimethylbut-$3^1$-enyl)-4-pentynoic acid
2-($1^1$,$3^1$,dimethylbutyl)-4-pentynoic acid
2-($1^1$,$3^1$-dimethylbut-$1^1$-enyl)-4-pentynoic acid
2-($1^1$,$2^1$-dimethylbut-$2^1$-enyl)-4-pentynoic acid
2-($1^1$,$3^1$-dimethylbut-$3^1$-enyl)-4-pentynoic acid
2-($2^1$,$2^1$-dimethylbutyl)-4-pentynoic acid
2-($2^1$,$2^1$-dimethylbut-$3^1$-enyl)-4-pentynoic acid
2-($2^1$,$3^1$-dimethylbutyl)-4-pentynoic acid
2-($2^1$,$3^1$-dimethylbut-$1^1$-enyl)-4-pentynoic acid
2-($2^1$,$3^1$-dimethylbut-$2^1$-enyl)-4-pentynoic acid
2-($2^1$,$3^1$-dimethylbut-$3^1$-enyl)-4-pentynoic acid
2-($3^1$,$3^1$-dimethylbutyl)-4-pentynoic acid
2-($3^1$,$3^1$-dimethylbut-$1^1$-enyl)-4-pentynoic acid
2-($1^1$,$1^1$,$2^1$-trimethylpropyl)-4-pentynoic acid 2-($1^1$,$1^1$,$2^1$-trimethylprop-$2^1$-enyl)-4-pentynoic acid
2-($1^1$,$2^1$,$2^1$-trimethylpropyl)-4-pentynoic acid
2-n-heptyl-4-pentynoic acid
2-)$1^1$-methylhexyl)-4-pentynoic acid
2-($2^1$-methylhexyl)-4-pentynoic acid
2-($3^1$-methylhexyl)-4-pentynoic acid
2-($4^1$-methylhexyl)-4-pentynoic acid
2-($5^1$-methylhexyl)-4-pentynoic acid
2-($1^1$,$1^1$-dimethylpentyl)-4-pentynoic acid
2-($1^1$,$2^1$-dimethylpentyl)-4-pentynoic acid
2-($1^1$,$3^1$-dimethylpentyl)-4-pentynoic acid
2-($1^1$,$4^1$-dimethylpentyl)-4-pentynoic acid
2-($2^1$,$2^1$-dimethylpentyl)-4-pentynoic acid
2-($2^1$,$3^1$-dimethylpentyl)-4-pentynoic acid
2-($2^1$,$4^1$-dimethylpentyl)-4-pentynoic acid
2-($3^1$,$3^1$-dimethylpentyl)-4-pentynoic acid
2-($3^1$,$4^1$-dimethylpentyl)-4-pentynoic acid
2-($4^1$,$4^1$-dimethylpentyl)-4-pentynoic acid
2-($1^1$,$1^1$,$2^1$-trimethylbutyl)-4-pentynoic acid
2-($1^1$,$1^1$,$3^1$-trimethylbutyl)-4-pentynoic acid
2-($1^1$,$2^1$,$3^1$-trimethylbutyl)-4-pentynoic acid
2-($2^1$,$2^1$,$3^1$-trimethylbutyl)-4-pentynoic acid
2-($2^1$,$3^1$,$3^1$-trimethylbutyl)-4-pentynoic acid.]

[8. The compounds according to claim 7 selected from the group consisting of 2-n-butyl-4-pentynoic acid, 2-n-pentyl-4- pentynoic acid and 2-n-hexyl-4-pentynoic acid.]

[9. The compounds according to claim 8 wherein the compounds are selected from the group consisting of 2-n-pentyl-4-pentynoic acid and 2-n-hexyl-4-pentynoic acid.]

[10. A method of preparing compounds having the general formula (I)

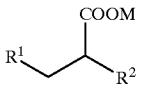

wherein $R^1$ is —C≡CH, —CH═$CH_2$, or —$CH_2$—$CH_3$, $R^2$ is saturated, unsaturated, branched and/or unbranched $C_{1-30}$ alkyl group, optionally substituted with an aliphatic of aromatic $C_{3-9}$ cyclohydrocarbon or heterocyclic group; and M is a hydrogen or a metal atom, comprising;

combining a malonic acid diester with a first halide having the general formula (VII)

$$R^2—X \quad (VII)$$

wherein $R^2$ has the meaning given previously; or halogen, to form a 2-alkyl malonic acid diester, and combining the 2-alkyl malonic acid diester with a second halide having the general formula (VIII)

$$R^1—CH_2—X \quad (VIII)$$

wherein $R^1$ has the meaning given previously; or combining the malonic acid diester with the second halide having the general formula (VIII) to form a 2-alkyl malonic acid diester; and combining the first halide having the general formula (VII) to form a compound of formula (IX)

(IX)

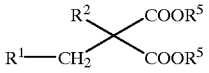

wherein $R^5$ is an alkyl group; and hydrolyzing and decarboxylating the compound of formula (IX) to form the compound of formula (I) to a salt.]

[11. The method according to claim 10 wherein $R^1$ is —C≡CH and $R^2$ is —$(CH_2)_{1-9}$—$CH_3$.]

[12. The method according to claim 11 wherein $R^2$ is —$(CH_2)_{3-6}$—$CH_3$).]

[13. The method according to claim 12 wherein $R^2$ is —$(CH_2)_{4-5}$—$CH_3$.]

[14. The method according to claim 10 wherein the method is used to prepare a compound selected from the group consisting of:

2-n-prop-$1^1$-enyl-4-pentynoic acid
2-n-prop-$2^1$-enyl-4-pentynoic acid
2-i-propyl-4-pentynoic acid
2-i-propenyl-4-pentynoic acid
2-n-butyl-4-pentynoic acid
2-n-but-$1^1$-enyl-4-pentynoic acid
2-n-but-$2^1$-enyl-4-pentynoic acid
2-n-but-$3^1$-enyl-4-pentynoic acid
2-($1^1$-methylbutyl)-4-pentynoic acid
2-($1^1$-methylprop-$2^1$-enyl)-4-pentynoic acid
2-($1^1$-methylprop-$2^1$-enyl)-4-pentynoic acid
2-($2^1$-methylpropyl)-4-pentynoic acid
2-($2^1$-methylprop-$1^1$-enyl)-4-pentynoic acid
2-($2^1$-methylprop-$2^1$-enyl)-4-pentynoic acid
2-tert.-butyl-4-pentynoic acid
2-n-pentyl-4-pentynoic acid
2-($1^1$-methylbutyl)-4-pentynoic acid
2-($2^1$-methylbutyl)-4-pentynoic acid
2-($3^1$-methylbutyl)-4-pentynoic acid
2-($1^1$,$1^1$-dimethylpropyl)-4-pentynoic acid
2-($1^1$,$2^1$-dimethylpropyl)-4-pentynoic acid
2-($2^1$,$2^1$-dimethylpropyl)-4-pentynoic acid
2-n-hexyl-4-pentynoic acid
2-n-hex-$1^1$-enyl-4-pentynoic acid
2-n-hex-$2^1$-enyl-4-pentynoic acid
2-n-hex-$3^1$-enyl-4-pentynoic acid
2-n-hex-$4^1$-enyl-4-pentynoic acid
2-n-hex-$5^1$-enyl-4-pentynoic acid
2-($1^1$-methylpentyl)-4-pentynoic acid
2-($1^1$-methylpent-$1^1$-enyl)-4-pentynoic acid
2-($1^1$-methylpent-$2^1$-enyl)-4-pentynoic acid
2-($1^1$-methylpent-$3^1$-enyl)-4-pentynoic acid
2-($1^1$-methylpent-$4^1$-enyl)-4-pentynoic acid
2-($2^1$-methylpentyl)-4-pentynoic acid
2-($2^1$-methylpent-$1^1$-enyl)-4-pentynoic acid
2-($2^1$-methylpent-$2^1$-enyl)-4-pentynoic acid
2-($2^1$-methylpent-$3^1$-enyl)-4-pentynoic acid
2-($2^1$-methylpent-$4^1$-enyl)-4-pentynoic acid
2-($3^1$-methylpentyl)-4-pentynoic acid
2-($3^1$-methylpent-$1^1$-enyl)-4-pentynoic acid
2-($3^1$-methylpent-$2^1$-enyl)-4-pentynoic acid 2-($3^1$-methylpent-$3^1$-enyl)-4-pentynoic acid
2-($3^1$-methylpent-$4^1$-enyl)-4-pentynoic acid
2-($4^1$-methylpentyl)-4-pentynoic acid
2-($4^1$-methylpent-$1^1$-enyl)-4-pentynoic acid
2-($4^1$-methylpent-$2_1$-enyl)-4-pentynoic acid
2-($4^1$-methylpent-$3^1$-enyl)-4-pentynoic acid
2-($4^1$-methylpent-$4^1$-enyl)-4-pentynoic acid
2-($1^1$,$1^1$-dimethylbutyl)-4-pentynoic acid
2-($1^1$,$1^1$-dimethylbut-$2^1$-enyl)-4-pentynoic acid
2-($1^1$,$1^1$-dimethylbut-$3^1$-enyl)-4-pentynoic acid
2-($1^1$,$2^1$-dimethylbutyl)-4-pentynoic acid
2-($1^1$,$2^1$-dimethylbut-$1^1$-enyl)-4-pentynoic acid
2-($1^1$,$2^1$,dimethylbut-$2^1$-enyl)-4pentynoic acid
2-($1^1$,$2^1$,dimethylbut-$3^1$-enyl)-4-pentynoic acid
2-($1^1$,$3^1$-dimethylbutyl)-4-pentynoic acid
2-($1^1$,$3^1$-dimethylbut-$1^1$-enyl)-4-pentynoic acid
2-($1^1$,$3^1$-dimethylbut-$2^1$-enyl)-4-pentynoic acid
2-($1^1$,$3^1$-dimethylbut-$3^1$-enyl)-4-pentynoic acid
2-($2^1$,$2^1$-dimethylbutyl)-4-pentynoic acid
2-($2^1$,$2^1$-dimethylbut-$3^1$-enyl)-4-pentynoic acid
2-($2^1$,$3^1$-dimethylbutyl)-4-pentynoic acid
2-($2^1$,$3^1$-dimethylbut-$1^1$-enyl)-4-pentynoic acid
2-($2^1$,$3^1$-dimethylbut-$2^1$-enyl)-4-pentynoic acid
2-($2^1$,$3^1$-dimethylbut-$3^1$-enyl)-4-pentynoic acid
2-)$3^1$,$3^1$-dimethylbutyl)-4-pentynoic acid
2-($3^1$,$3^1$-dimethylbut-$1^1$-enyl)-4-pentynoic acid
2-($1^1$,$1^1$,$2^1$-trimethylpropyl)-4-pentynoic acid
2-($1^1$,$1^1$,$2^1$-trimethylprop-$2^1$-enyl)-4-pentynoic acid
2-($1^1$,$2^1$,$2^1$-trimethylpropyl)-4-pentynoic acid
2-n-heptyl-4-pentynoic acid
2-)$1^1$-methylhexyl)-4-pentynoic acid
2-($2^1$-methylhexyl)-4-pentynoic acid
2-($3^1$-methylhexyl)-4-pentynoic acid
2-($4^1$-methylhexyl)-4-pentynoic acid
2-($5^1$-methylhexyl)-4-pentynoic acid
2-($1^1$,$1^1$-dimethylpentyl)-4-pentynoic acid
2-($1^1$,$2^1$-dimethylpentyl)-4-pentynoic acid
2-($1^1$,$3^1$-dimethylpentyl)-4-pentynoic acid
2-($1^1$,$4^1$-dimethylpentyl)-4-pentynoic acid
2-($2^1$,$2^1$-dimethylpentyl)-4-pentynoic acid
2-($2^1$,$3^1$-dimethylpentyl)-4-pentynoic acid
2-($2^1$,$4^1$-dimethylpentyl)-4-pentynoic acid
2-($3^1$,$3^1$-dimethylpentyl)-4-pentynoic acid
2-($3^1$,$4^1$-dimethylpentyl)-4-pentynoic acid
2-($4^1$,$4^1$-dimethylpentyl)-4-pentynoic acid
2-($1^1$,$1^1$,$2^1$-trimethylbutyl)-4-pentynoic acid
2-($1^1$,$1^1$,$3^1$-trimethylbutyl)-4-pentynoic acid
2-($1^1$,$2^1$,$3^1$-trimethylbutyl)-4-pentynoic acid
2-($2^1$,$2^1$,$3^1$-trimethylbutyl)-4-pentynoic acid
2-($2^{11}$,$3^1$,$3^1$-trimethylbutyl)-4-pentynoic acid.]

[15. The method according to claim 10 wherein the method is used to prepare at least one compound selected from the group consisting of 2-n-butyl-4-pentynoic acid, 2-n-pentyl-4-pentynoic acid and 2-n-hexyl-4-pentynoic acid.]

*16. A S-enantiomer of a compound of formula (I)*

(I)

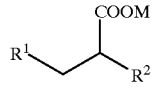

*wherein*

*$R^1$ is —C≡CH, $R^2$ is a saturated, unsaturated, branched and/or unbranched $C_1$–$C_{30}$ alkyl group, optionally further comprising an aliphatic or aromatic $C_{3-9}$ cyclo-hydrocarbon or heterocyclic group comprising 3 to 9 atoms; and M is a hydrogen or a metal atom, and pharmaceutical acceptable salts thereof; with the proviso that the compound of formula (I) is not 2-n-propyl-4-pentynoic acid.*

*17. A compound according to claim 16 wherein $R^2$ is —$(CH_2)_{3-6}$—$CH_3$.*

*18. A compound according to claim 16 wherein $R^2$ is —$(CH_2)_{4-5}$—$CH_3$.*

*19. A compound according to claim 16 selected from the group consisting of:*

*2-n-prop-$1^1$-enyl-4-pentynoic acid*
*2-n-prop-$2^1$-enyl-4-pentynoic acid*
*2-i-propyl-4-pentynoic acid*
*2-i-propenyl-4-pentynoic acid*
*2-n-butyl-4-pentynoic acid*
*2-n-but-$1^1$-enyl-4-pentynoic acid*
*2-n-but-$2^1$-enyl-4-pentynoic acid*
*2-n-but-$3^1$-enyl-4-pentynoic acid*
*2-($1^1$-methylbutyl)-4-pentynoic acid*
*2-($1^1$-methylprop-$1^1$-enyl)-4-pentynoic acid*
*2-($1^1$-methylprop-$2^1$-enyl)-4-pentynoic acid*
*2-($2^1$-methylpropyl)-4-pentynoic acid*
*2-($2^1$-methylprop-$1^1$-enyl)-4-pentynoic acid*
*2-($2^1$-methylprop-$2^1$-enyl)-4-pentynoic acid*
*2-tert.-butyl-4-pentynoic acid*
*2-n-pentyl-4-pentynoic acid*
*2-($1^1$-methylbutyl)-4-pentynoic acid*
*2-($2^1$-methylbutyl)-4-pentynoic acid*
*2-($3^1$-methylbutyl)-4-pentynoic acid*
*2-($1^1$,$1^1$-dimethylpropyl)-4-pentynoic acid*
*2-($1^1$,$2^1$-dimethylpropyl)-4-pentynoic acid*
*2-($2^1$,$2^1$-dimethylpropyl)-4-pentynoic acid*
*2-n-hexyl-4-pentynoic acid*
*2-n-hex-$1^1$-enyl-4-pentynoic acid*
*2-n-hex-$2^1$-enyl-4-pentynoic acid*
*2-n-hex-$3^1$-enyl-4-pentynoic acid*
*2-n-hex-$4^1$-enyl-4-pentynoic acid*
*2-n-hex-$5^1$-enyl-4-pentynoic acid*
*2-($1^1$-methylpentyl)-4-pentynoic acid*
*2-($1^1$-methylpent-$1^1$-enyl)-4-pentynoic acid*
*2-($1^1$-methylpent-$2^1$-enyl)-4-pentynoic acid*
*2-($1^1$-methylpent-$3^1$-enyl)-4-pentynoic acid*
*2-($1^1$-methylpent-$4^1$-enyl)-4-pentynoic acid*
*2-($2^1$-methylpentyl)-4-pentynoic acid*
*2-($2^1$-methylpent-$1^1$-enyl)-4-pentynoic acid*
*2-($2^1$-methylpent-$2^1$-enyl)-4-pentynoic acid*
*2-($2^1$-methylpent-$3^1$-enyl)-4-pentynoic acid*

2-($2^1$-methylpent-$4^1$-enyl)-4-pentynoic acid
2-($3^1$-methylpentyl)-4-pentynoic acid
2-($3^1$-methylpent-$1^1$-enyl)-4-pentynoic acid
2-($3^1$-methylpent-$2^1$-enyl)-4-pentynoic acid
2-($3^1$-methylpent-$3^1$-enyl)-4-pentynoic acid
2-($3^1$-methylpent-$4^1$-enyl)-4-pentynoic acid
2-($4^1$-methylpentyl)-4-pentynoic acid
2-($4^1$-methylpent-$1^1$-enyl)-4-pentynoic acid
2-($4^1$-methylpent-$2^1$-enyl)-4-pentynoic acid
2-($4^1$-methylpent-$3^1$-enyl)-4-pentynoic acid
2-($4^1$-methylpent-$4^1$-enyl)-4-pentynoic acid
2-($1^1$-$1^1$-dimethylbutyl)-4-pentynoic acid
2-($1^1$-$1^1$-dimethylbut-$1^1$-enyl)-4-pentynoic acid
2-($1^1$-$1^1$-dimethylbut-$3^1$-enyl)-4-pentynoic acid
2-($1^1$-$2^1$-dimethylbutyl)-4-pentynoic acid
2-($1^1$-$2^1$-dimethylbut-$1^1$-enyl)-4-pentynoic acid
2-($1^1$-$2^1$-dimethylbut-$2^1$-enyl)-4-pentynoic acid
2-($1^1$-$2^1$-dimethylbut-$3^1$-enyl)-4-pentynoic acid
2-($1^1$-$3^1$-dimethylbutyl)-4-pentynoic acid
2-($1^1$-$3^1$-dimethylbut-$1^1$-enyl)-4-pentynoic acid
2-($1^1$-$3^1$-dimethylbut-$2^1$-enyl)-4-pentynoic acid
2-($1^1$-$3^1$-dimethylbut-$3^1$-enyl)-4-pentynoic acid
2-($2^1$-$2^1$-dimethylbutyl)-4-pentynoic acid
2-($2^1$-$2^1$-dimethylbut-$3^1$-enyl)-4-pentynoic acid
2-($2^1$-$3^1$-dimethylbutyl)-4-pentynoic acid
2-($2^1$-$3^1$-dimethylbut-$1^1$-enyl)-4-pentynoic acid
2-($2^1$-$3^1$-dimethylbut-$2^1$-enyl)-4-pentynoic acid
2-($2^1$-$3^1$-dimethylbut-$3^1$-enyl)-4-pentynoic acid
2-($3^1$-$3^1$-dimethylbutyl)-4-pentynoic acid
2-($3^1$-$3^1$-dimethylbut-$1^1$-enyl)-4-pentynoic acid
2-($1^1$-$1^1$-$2^1$-trimethylpropyl)-4-pentynoic acid
2-($1^1$-$1^1$-$2^1$-trimethylprop-2-enyl)-4-pentynoic acid
2-($1^1$-$2^1$-$2^1$-trimethylpropyl)-4-pentynoic acid
2-n-heptyl-4-pentynoic acid
2-($1^1$-methylhexyl)-4-pentynoic acid
2-($2^1$-methylhexyl)-4-pentynoic acid
2-($3^1$-methylhexyl)-4-pentynoic acid
2-($4^1$-methylhexyl)-4-pentynoic acid
2-($5^1$-methylhexyl)-4-pentynoic acid
2-($1^1$,$1^1$-dimethylpentyl)-4-pentynoic acid
2-($1^1$,$2^1$-dimethylpentyl)-4-pentynoic acid
2-($1^1$,$3^1$-dimethylpentyl)-4-pentynoic acid
2-($1^1$,$4^1$-dimethylpentyl)-4-pentynoic acid
2-($2^1$,$2^1$-dimethylpentyl)-4-pentynoic acid
2-($2^1$,$3^1$-dimethylpentyl)-4-pentynoic acid
2-($2^1$,$4^1$-dimethylpentyl)-4-pentynoic acid
2-($3^1$,$3^1$-dimethylpentyl)-4-pentynoic acid
2-($3^1$,$4^1$-dimethylpentyl)-4-pentynoic acid
2-($4^1$,$4^1$-dimethylpentyl)-4-pentynoic acid
2-($1^1$,$1^1$,$2^1$-trimethylbutyl)-4-pentynoic acid
2-($1^1$,$1^1$,$3^1$-trimethylbutyl)-4-pentynoic acid
2-($1^1$,$2^1$,$3^1$-trimethylbutyl)-4-pentynoic acid
2-($2^1$,$2^1$,$3^1$-trimethylbutyl)-4-pentynoic acid
2-($2^1$,$3^1$,$3^1$-trimethylbutyl)-4-pentynoic acid.

20. A compound according to claim 19 wherein the compounds are selected from the group consisting of 2-n-pentyl-4-pentynoic acid and 2-n-hexyl-4-pentynoic acid.

21. 2-n-pentyl-4-pentynoic acid and enantiomers thereof and pharmaceutically acceptable salts thereof.

22. A S-enantiomer of the compounds of claim 21 and pharmaceutically acceptable salts thereof.

23. A method of preparing a compound having the general formula (I)

(I)

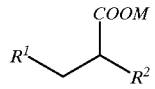

wherein $R^1$ is —C≡CH, $R^2$ is a saturated, unbranched $C_5$ alkyl group; and M is a hydrogen or a metal atom, comprising:

combining a malonic acid diester with a first halide having the general formula (VII)

$$R^2—X \quad (VII)$$

wherein $R^2$ has the meaning given previously to form a 2-pentyl malonic acid diester, and combining the 2-pentyl malonic acid diester with a second halide having the general formula (VIII)

$$R^1—CH_2—X \quad (VIII)$$

wherein $R^1$ has the meaning given previously; or combining the malonic acid diester with the second halide having the general formula (VIII) to form a 2-pentyl malonic acid diester; and combining the first halide having the general formula (VII) to form a compound of formula (IX)

(IX)

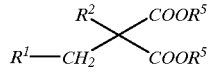

wherein $R^5$ is an alkyl group; and hydrolyzing and decarboxylating the compound of formula (IX) to form the compound of formula (I); and optionally converting the compound of formula (I) to a salt.

* * * * *